(12) United States Patent
Mitsumori et al.

(10) Patent No.: US 11,881,304 B2
(45) Date of Patent: Jan. 23, 2024

(54) MEDICAL INFORMATION PROCESSING APPARATUS AND MEDICAL INFORMATION PROCESSING SYSTEM

(71) Applicant: CANON MEDICAL SYSTEMS CORPORATION, Otawara (JP)

(72) Inventors: Keita Mitsumori, Nasushiobara (JP); Yasuhito Nagai, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 650 days.

(21) Appl. No.: 16/892,388

(22) Filed: Jun. 4, 2020

(65) Prior Publication Data

US 2020/0402650 A1     Dec. 24, 2020

(30) Foreign Application Priority Data

Jun. 18, 2019   (JP) .................................. 2019-113039

(51) Int. Cl.
*G06N 5/043* (2023.01)
*G16H 40/20* (2018.01)
(Continued)

(52) U.S. Cl.
CPC ............. *G16H 40/20* (2018.01); *G06N 5/043* (2013.01); *G06N 20/20* (2019.01); *G16H 40/60* (2018.01); *G06N 5/00* (2013.01); *G06N 7/00* (2013.01)

(58) Field of Classification Search
CPC .................... G06N 5/00–48; G06N 20/00–20
(Continued)

(56) References Cited

U.S. PATENT DOCUMENTS 10,810,491 B1 * 10/2020 Xia .......................... G06N 3/04
11,537,439 B1 * 12/2022 Liberty ................. G06F 9/5077
(Continued)

FOREIGN PATENT DOCUMENTS

| JP | 2017-004509 A | 1/2017 |
| JP | 2018-206016 A | 12/2018 |
| WO | WO 2018/098039 A1 | 5/2018 |

OTHER PUBLICATIONS

Sheller et al. "Multi-Institutional Deep Learning Modeling without sharing Patient Data: A Feasibility Study on Brain Tumor Segmentation" Oct. 2018, arXiv:1810.04304v2.*
(Continued)

*Primary Examiner* — Jue Louie
(74) *Attorney, Agent, or Firm* — Oblon, McClelland, Maier & Neustadt, L.L.P.

(57) ABSTRACT

A medical information processing apparatus according to an embodiment includes a processing circuitry. The processing circuitry is configured: to distribute, to an information processing apparatus provided at each of a plurality of medical institutions, a program for causing a machine learning process to be executed by using medical data held at the medical institution having the information processing apparatus; to receive, from each of the information processing apparatuses, a change amount in a parameter related to the machine learning process, regarding a change caused in conjunction with the execution of the machine learning process; to adjust a value of the parameter on the basis of the received change amount; and to transmit the adjusted parameter to each of the information processing apparatuses to cause the machine learning process to be executed on the basis of the parameter.

8 Claims, 9 Drawing Sheets

(51) Int. Cl.
  *G16H 40/60* (2018.01)
  *G06N 20/20* (2019.01)
  *G06N 5/00* (2023.01)
  *G06N 7/00* (2023.01)

(58) Field of Classification Search
  USPC .................................................. 706/10–12
  See application file for complete search history.

(56) References Cited

U.S. PATENT DOCUMENTS

| | | | |
|---|---|---|---|
| 2014/0088989 A1* | 3/2014 | Krishnapuram | G16H 50/50 705/2 |
| 2017/0372230 A1* | 12/2017 | Kuromatsu | G06N 20/00 |
| 2018/0144244 A1* | 5/2018 | Masoud | G06N 3/105 |
| 2018/0285694 A1* | 10/2018 | Kobayashi | G06F 15/76 |
| 2019/0227980 A1* | 7/2019 | McMahan | G06N 3/0445 |
| 2019/0311220 A1* | 10/2019 | Hazard | G06K 9/6257 |
| 2019/0385043 A1* | 12/2019 | Choudhary | G06N 3/084 |
| 2020/0042362 A1* | 2/2020 | Cui | G06F 12/0207 |
| 2020/0302234 A1* | 9/2020 | Walters | G06K 9/6276 |
| 2020/0334567 A1* | 10/2020 | Bhattacharjee | H04L 67/125 |
| 2021/0287080 A1* | 9/2021 | Moloney | G06V 10/95 |

OTHER PUBLICATIONS

Notice of Reasons for Refusal dated Jul. 4, 2023, in Japanese Patent Application No. 2019-113039 filed Jun. 18. 2019, citing documents 15-16 therein, 2 pages.

* cited by examiner

MEDICAL INFORMATION PROCESSING APPARATUS AND MEDICAL INFORMATION PROCESSING SYSTEM

CROSS-REFERENCE TO RELATED APPLICATIONS

This application is based upon and claims the benefit of priority from Japanese Patent Application No. 2019-113039, filed on Jun. 18, 2019; the entire contents of which are incorporated herein by reference.

FIELD

Embodiments described herein relate generally to a medical information processing apparatus and a medical information processing system.

BACKGROUND

In recent years, the artificial intelligence (AI) (machine learning) technology has been used in various systems and has also increasingly been applied to the medical industry. For example, if in specific medical cases, a known model (trained model) is capable of detecting abnormality locations more quickly and more precisely than interpreting doctors.

To create a model, it is necessary to acquire a large amount of data to be used in machine learning. It is, however, difficult to acquire such a large amount of medical data from one medical institution. To cope with this situation, it may be possible to use a method by which a trained model is created by aggregating medical data from a plurality of medical institutions in one location. However, because medical data contains personal information of the patients, taking medical data to the outside involves a security issue. Also, because medical data is assets intrinsic to medical institutions, there is a possibility that it may not be allowed to take medical data to the outside.

Further, a technique has hitherto been proposed by which machine learning processes of a decentralized type are performed in parallel, by using a plurality of workers that are communicably connected. According to this technique, by transmitting and receiving a parameter used for the learning, the individual workers are each able to create a model, without each worker sending the data used in the learning to the outside.

According to the aforementioned conventional technique, however, it is necessary to tune the execution environments, the parameters, and the like to be the same among the workers, at the start of the machine learning. A problem thus arises where the preparation can be cumbersome. Further, because this technique is not expected to be applied to medical institutions, there is room for further improvements.

DETAILED DESCRIPTION

A medical information processing apparatus according to an embodiment includes a processing circuitry. The processing circuitry is configured: to distribute, to an information processing apparatus provided at each of a plurality of medical institutions, a program for causing a machine learning process to be executed by using medical data held at the medical institution having the information processing apparatus; to receive, from each of the information processing apparatuses, a change amount in a parameter related to the machine learning process, regarding a change caused in conjunction with the execution of the machine learning process; to adjust a value of the parameter on the basis of the received change amount; and to transmit the adjusted parameter to each of the information processing apparatuses to cause the machine learning process to be executed on the basis of the parameter.

Exemplary embodiments of a medical information processing apparatus and a medical information processing method will be explained below, with reference to the accompanying drawings.

Figure 1:
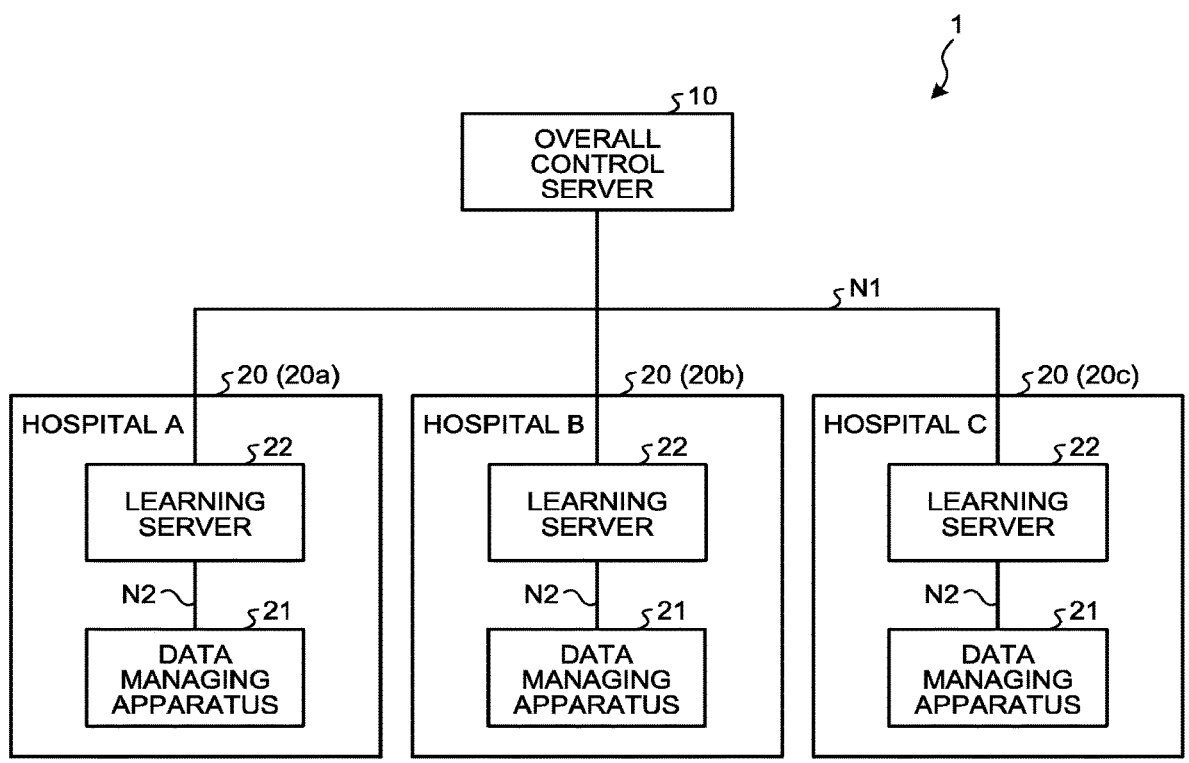
FIG. 1 is a diagram illustrating an exemplary configuration of a medical information processing system according to an embodiment.

FIG. 1 is a diagram illustrating an exemplary configuration of a medical information processing system according to an embodiment. As illustrated in FIG. 1, a medical information processing system 1 includes an overall control server 10 and a plurality of medical institution systems 20 (20*a* to 20*c*). The overall control server 10 and the medical institution systems 20 are communicably connected, for example, via a network N1 realized with an intranet, a dedicated communication line, or the like. In this situation, the number of medical institution systems 20 connected to the network N1 is not particularly limited.

The overall control server 10 is an example of the medical information processing apparatus. The overall control server 10 is communicably connected, via the network N1, to learning servers 22 each of which is provided in a different one of the medical institution systems 20. The overall control server 10 is configured to unitarily manage machine learning of a decentralized type (which hereinafter may be referred to as "decentralized machine learning") that uses the learning servers 22. For example, the overall control server 10 is realized by using a computer device such as a workstation, a server apparatus, or the like. Further, the overall control server 10 may be realized with a plurality of computer devices (a cloud) that uses cloud computing.

Each of the medical institution systems 20 is a system provided in a medical institution such as a hospital. In the example in FIG. 1, the medical institution system 20a is a medical institution system of hospital A. The medical institution system 20b is a medical institution system of hospital B. The medical institution system 20c is a medical institution system of hospital C.

Each of the medical institution systems 20 includes a data managing apparatus 21 and a different one of the learning servers 22. The data managing apparatus 21 and the learning server 22 are communicably connected to each other via a network N2 realized with a Local Area Network (LAN) or the like. Further, via a network device such as a router, the learning server 22 is connected to the network N1.

For example, the data managing apparatus 21 may be a Picture Archiving and Communication System (PACS) and is configured to store therein and manage medical data obtained at the host medical institution thereof. For example, the data managing apparatus 21 is configured to store therein, as the medical data, image data of patients taken (imaged) by using any of modalities such as Computerized Tomography (CT), Magnetic Resonance Imaging (MRI), and the like. Further, the data managing apparatus 21 is configured to store therein, as the medical data, physical information (age, gender, weight, etc.), electronic medical records, diagnosis/treatment records, and the like of the patients. In this situation, the data managing apparatus 21 is configured to manage the medical data of each of the patients so as to be kept in correspondence with an identifier identifying the patient.

The learning server 22 is an example of the information processing apparatus. Under control of the overall control server 10, by performing a machine learning process by using the medical data stored in the data managing apparatus 21, the learning server 22 is configured to create a model (a trained model) related to assisting diagnosing processes of medical doctors and the like. For example, the learning server 22 is realized by using a computer device such as a workstation or a server apparatus.

Figure 2:
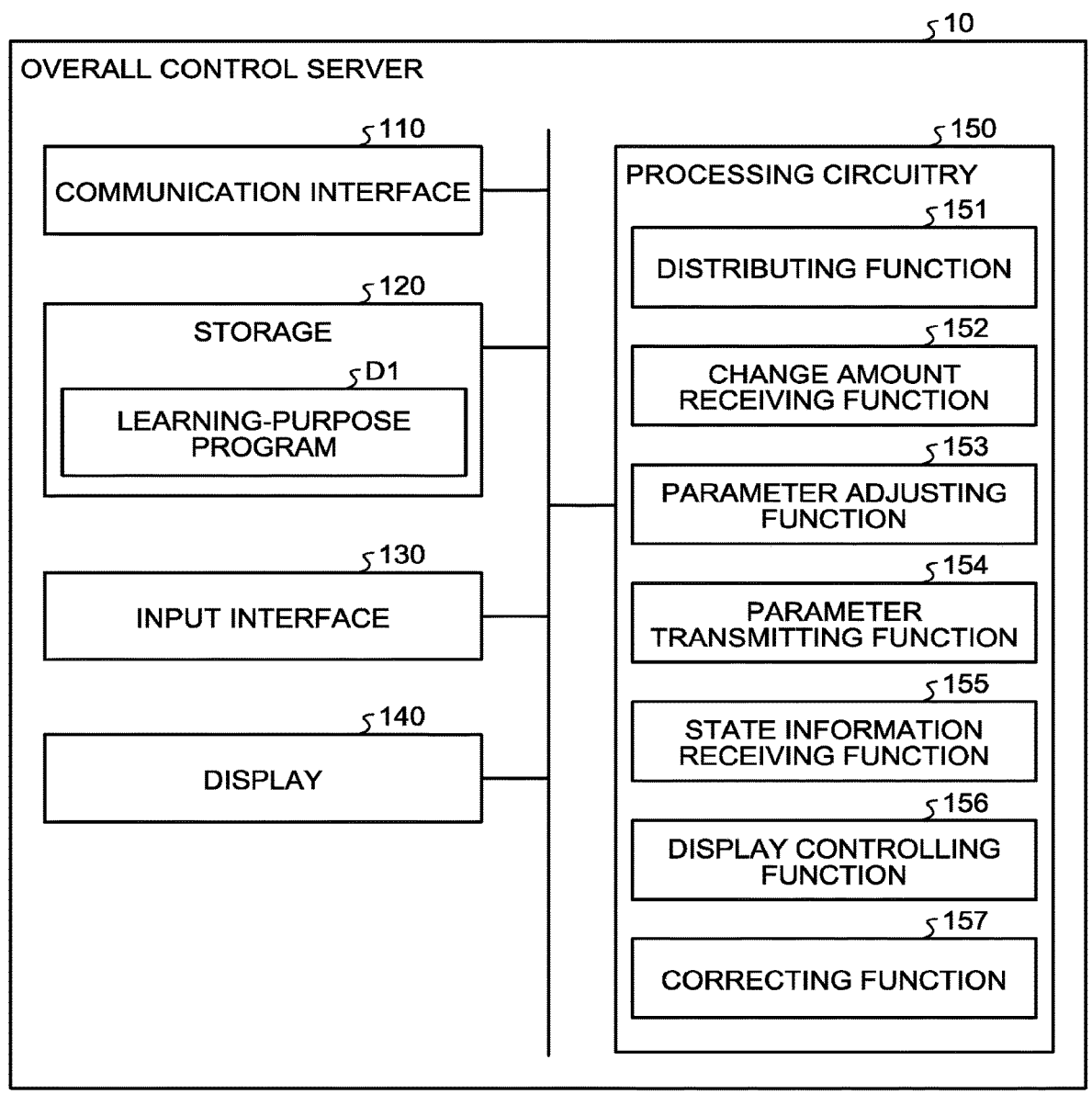
FIG. 2 is a diagram illustrating an exemplary configuration of an overall control server according to the embodiment.

Next, a configuration of the overall control server 10 will be explained. FIG. 2 is a diagram illustrating an exemplary configuration of the overall control server 10. As illustrated in FIG. 2, the overall control server 10 includes a communication interface 110, a storage 120, an input interface 130, a display 140, and a processing circuitry 150.

The communication interface 110 is connected to the processing circuitry 150 and is configured to control transfer of various types of data to and from, and communication performed with, each of the learning servers 22 connected to the network N1. For example, the communication interface 110 is realized by using a network card, a network adaptor, a Network Interface Controller (NIC), or the like.

The storage 120 is connected to the processing circuitry 150 and is configured to store various types of data therein. For example, the storage 120 is realized by using a semiconductor memory element such as a Random Access Memory (RAM) or a flash memory, or a hard disk, an optical disk, or the like.

More specifically, the storage 120 is configured to store therein various types of programs and setting information, in addition to an Operating System (OS) of the overall control server 10. Further, the storage 120 is configured to store therein a learning-purpose program D1 for machine learning purposes that is to be distributed to each of the learning servers 22.

The learning-purpose program D1 is a program for causing each of the learning servers 22 to perform the machine learning process. The learning-purpose program D1 includes, for example, a prototype model (which hereinafter may be referred to as a model) serving as a prototype of the trained model and a program for performing a machine learning process of a decentralized type. The prototype model is a model which is designed for specific medical data subject to the machine learning process and in which a parameter such as a weight coefficient W (explained later) is set to an initial value.

The medical data used by the prototype model in the machine learning process is not particularly limited and may be any type of medical data. For example, the prototype model may be a model that, while using image data of a patient's head taken by CT or the like and a result of a diagnosis (e.g., an electronic medical record) made by a medical doctor on the image data as learning-purpose medical data, learns a relationship between these pieces of medical data through machine learning. In that situation, the result of the diagnosis made by the medical doctor is input as training data.

Further, the data form of the learning-purpose program D1 is not particularly limited. For example, the learning-purpose program D1 may be an application program that is executable when being introduced (installed) in any of the learning servers 22. Alternatively, the learning-purpose program D1 may be a hypervisor image data that can be caused to work as a virtual machine in the OS of any of the learning servers 22. In another example, the learning-purpose program D1 may be image data of Docker (registered trademark) or the like that shares the kernels of the learning servers 22 and is capable of executing processes in units called containers.

The input interface 130 is connected to the processing circuitry 150 and is configured to receive operations to input various types of instructions and various types of information from an operator. More specifically, the input interface 130 is configured to convert the input operations received from the operator into electrical signals and to output the electrical signals to the processing circuitry 150. For example, the input interface 130 is realized by using a trackball, a switch button, a mouse, a keyboard, a touchpad on which input operations are performed by touching an operation surface thereof, a touch screen in which a display screen and a touchpad are integrally formed, a contactless input circuit using an optical sensor, an audio input circuit, and/or the like. The input interface 130 does not necessarily have to include physical operation component parts such as a mouse, a keyboard, and/or the like. Possible examples of the input interface 130 include an electrical signal processing circuit configured to receive an electrical signal corresponding to an input operation from an external input device provided separately from the apparatus and to output the received electrical signal to a controlling circuit.

The display 140 is connected to the processing circuitry 150 and is configured to display various types of information and various types of images. More specifically, the display 140 is configured to convert data of the various types of information and the various types of images sent thereto from the processing circuitry 150 into display-purpose electrical signals and to output the display-purpose electrical signals. For example, the display 140 is realized by using a liquid crystal monitor, a Cathode Ray Tube (CRT) monitor, a touch panel, or the like.

The processing circuitry 150 is configured to integrally control operations of the overall control server 10. More specifically, the processing circuitry 150 is configured to store the medical data output from the communication interface 110 into the storage 120. Further, the processing circuitry 150 is configured to read any of the medical data from the storage 120 and to cause the display 140 to display the medical data. For example, the processing circuitry 150 is realized by using a processor.

Further, the overall control server 10 includes a distributing function 151, a change amount receiving function 152, a parameter adjusting function 153, a parameter transmitting function 154, a state information receiving function 155, a display controlling function 156, and a correcting function 157.

In the overall control server 10, the functions are stored in the storage 120 in the form of computer-executable programs. The processing circuitry 150 is a processor configured to realize the functions corresponding to the programs by reading and executing the programs from the storage 120. In other words, the processing circuitry 150 that has read the programs has the functions corresponding to the read programs.

With reference to FIG. 2, the example was explained in which the single processing circuit (the processing circuitry 150) realizes the distributing function 151, the change amount receiving function 152, the parameter adjusting function 153, the parameter transmitting function 154, the state information receiving function 155, the display controlling function 156, and the correcting function 157; however, it is also acceptable to structure the processing circuitry 150 by combining together a plurality of independent processors so that the functions are realized as a result of the processors executing the programs. Further, the functions of the processing circuitry 150 may be realized as being distributed among or integrated into one or more processing circuits, as appropriate.

The distributing function 151 is configured to distribute (transmit) the learning-purpose program D1 stored in the storage 120 to each of the learning servers 22 via the communication interface 110. In this situation, to each of the learning servers 22, the same learning-purpose program D1 is distributed. In each of the learning servers 22 having received the distribution of the learning-purpose program D1, an execution environment where the machine learning process is executable is realized as a result of the learning-purpose program D1 being introduced (installed, deployed, or the like). In other words, in the learning servers 22, mutually the same execution environment is realized.

In this situation, the timing and the method for distributing the learning-purpose program D1 are not particularly limited. For example, the distributing function 151 may be configured to unsolicitedly distribute the learning-purpose program D1 to each of the learning servers 22 or may be configured to distribute the learning-purpose program D1 in response to requests from the learning servers 22.

Via the communication interface 110, the change amount receiving function 152 is configured to receive a change amount transmitted from each of the learning servers 22. In this situation, the change amount denotes a change amount in a parameter related to the machine learning process, regarding a change caused in conjunction with the execution of the machine learning process. For example, in deep learning and neural networks, the parameter corresponds to a weight coefficient W, whereas the change amount corresponds to a change amount ΔW of the weight coefficient W. In the following sections, an example will be explained in which the parameter is the "weight coefficient W", whereas the change amount is the "change amount ΔW".

The parameter adjusting function 153 is configured to determine a new weight coefficient W, by adjusting a previous weight coefficient W, on the basis of the change amount ΔW received by the change amount receiving function 152. In this situation, the method for adjusting the weight coefficient W is not particularly limited, and a publicly-known method may be used. In one example, the new weight coefficient W may be determined as a value obtained by subtracting the product of the change amount ΔW and a learning coefficient, from the previous weight coefficient W. The learning coefficient may be a fixed value or may be a dynamic value that varies according to the number of times the machine learning process is performed. In another example, the new weight coefficient W may be determined as a value obtained by subtracting an average value or a weighted average value of change amounts ΔW obtained from the learning servers 22, from the previous weight coefficient W.

The parameter transmitting function 154 is configured to transmit the new weight coefficient W determined by the parameter adjusting function 153 to each of the learning servers 22 via the communication interface 110. In this situation, the weight coefficient W is individually transmitted to each of the learning servers 22.

Via the communication interface 110, the state information receiving function 155 is configured to receive information (hereinafter, "state information") having been transmitted thereto from each of the learning servers 22 and indicating the state of the machine learning process. On the basis of the state information received by the state information receiving function 155, the display controlling function 156 is configured to cause the display 140 to display the state of the machine learning process performed in each of the learning servers 22. Further, in response to an input operation received via the input interface 130, the correcting function 157 is configured to perform a process for correcting (changing) conditions related to the machine learning process. Operations of the display controlling function 156 and the correcting function 157 will be explained later.

Figure 3:
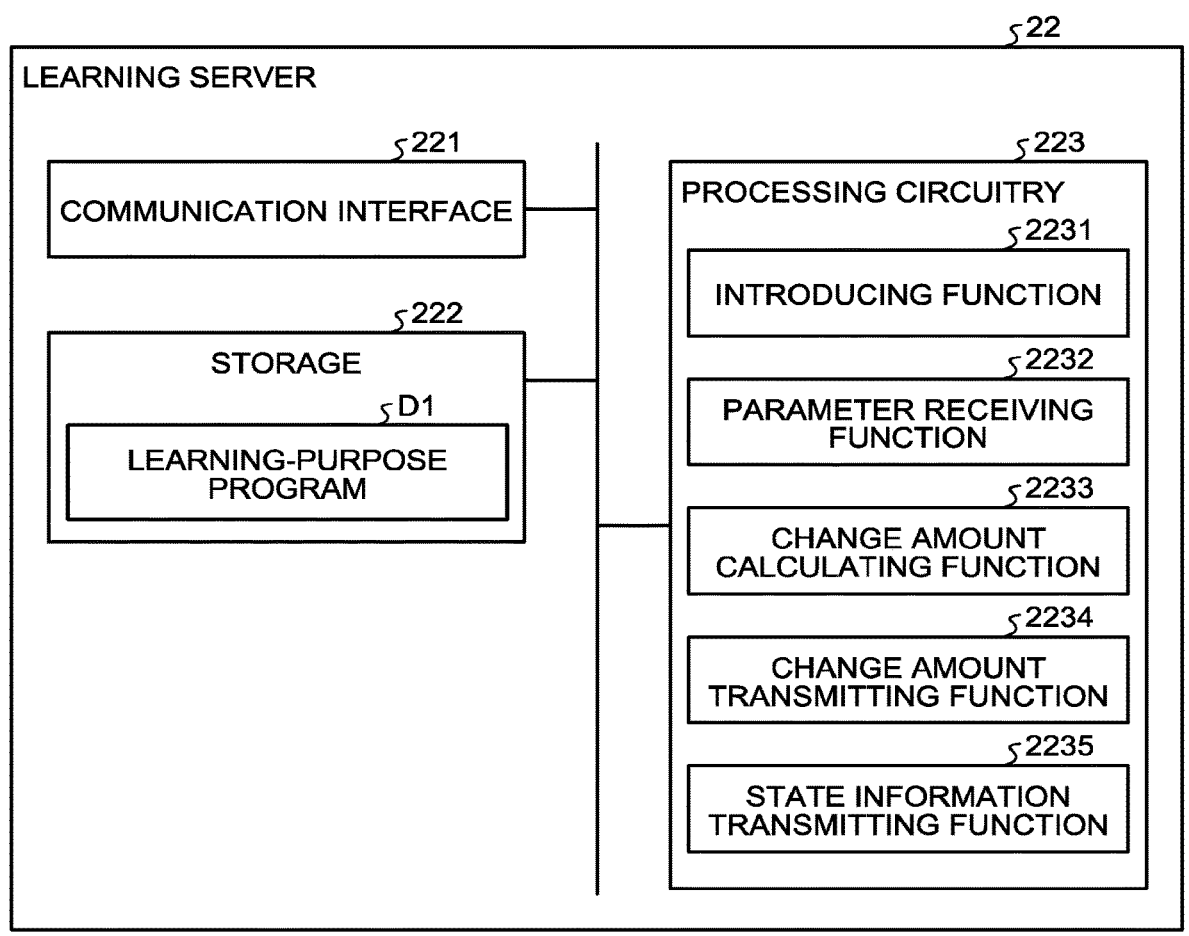
FIG. 3 is a diagram illustrating an exemplary configuration of any of learning servers according to the embodiment.

Next, a configuration of the learning servers 22 will be explained. FIG. 3 is a diagram illustrating an exemplary configuration of any of the learning servers 22. As illustrated in FIG. 3, the learning server 22 includes a communication interface 221, a storage 222, and a processing circuitry 223.

The communication interface 221 is connected to the processing circuitry 223 and is configured to control transfer of various types of data to and from, and communication performed with, the overall control server 10 connected to the network N1. Further, the communication interface 221 is configured to control transfer of various types of data to and from, and communication performed with, the data managing apparatus 21 connected to the network N2. For example, the communication interface 221 is realized by using a network card, a network adaptor, an NIC, or the like.

The storage 222 is connected to the processing circuitry 223 and is configured to store therein various types of data. For example, the storage 222 is realized by using a semiconductor memory element such as a RAM or a flash memory, or a hard disk, an optical disk, or the like.

More specifically, the storage 222 is configured to store therein various types of programs and setting information, in addition to an OS of the learning server 22. Further, the storage 222 is configured to store therein the learning-purpose program D1 distributed from the overall control server 10.

The processing circuitry 223 is configured to integrally control operations of the learning server 22. For example, the processing circuitry 223 is realized by using a processor.

Further, the learning server 22 includes an introducing function 2231, a parameter receiving function 2232, a change amount calculating function 2233, a change amount transmitting function 2234, and a state information transmitting function 2235.

In the learning server 22, the functions are stored in the storage 222 in the form of computer-executable programs. The processing circuitry 223 is a processor configured to realize the functions corresponding to the programs by reading and executing the programs from the storage 222. In other words, the processing circuitry 223 that has read the programs has the functions corresponding to the read programs. For example, among the abovementioned functions, the parameter receiving function 2232, the change amount calculating function 2233, the change amount transmitting function 2234, and the state information transmitting function 2235 are realized by the learning-purpose program D1. In other words, the learning servers 22 are provided with mutually the same functions, by the learning-purpose program D1 offered from the overall control server 10.

With reference to FIG. 3, the example was explained in which the single processing circuit (the processing circuitry 223) realizes the introducing function 2231, the parameter receiving function 2232, the change amount calculating function 2233, the change amount transmitting function 2234, and the state information transmitting function 2235; however, it is also acceptable to structure the processing circuitry 223 by combining together a plurality of independent processors so that the functions are realized as a result of the processors executing the programs. Further, the functions of the processing circuitry 223 may be realized as being distributed among or integrated into one or more processing circuits, as appropriate.

Via the communication interface 221, the introducing function 2231 is configured to receive the learning-purpose program D1 distributed from the overall control server 10. Further, by storing the received learning-purpose program D1 into the storage 222 and introducing (installing, deploying, or the like) the learning-purpose program D1 to the host device thereof, the introducing function 2231 is configured to realize the environment where the machine learning process is executable.

Via the communication interface 221, the parameter receiving function 2232 is configured to receive the weight coefficient W transmitted from the overall control server 10. On the basis of the weight coefficient W received by the parameter receiving function 2232, the change amount calculating function 2233 is configured to calculate the change amount ΔW of the weight coefficient W, by performing the machine learning process using the medical data managed by the data managing apparatus 21 of the host medical institution system 20 thereof. Via the communication interface 221, the change amount transmitting function 2234 is configured to transmit the change amount ΔW calculated by the change amount calculating function 2233 to the overall control server 10.

The method for calculating the change amount ΔW is not particularly limited, and a publicly-known method may be used. For example, the change amount ΔW may be calculated by using a stochastic gradient descent method, a backpropagation method, a quasi-Newton method, a genetic algorithm, or the like. Further, the timing with which the change amount calculating function 2233 transmits the change amount ΔW is not particularly limited. For example, the change amount transmitting function 2234 may be configured to transmit a change amount ΔW every time the change amount calculating function 2233 has machine-learned one hundred pieces of medical data.

Via the communication interface 221, the state information transmitting function 2235 is configured to transmit the state information indicating the state of the machine learning process performed by the change amount calculating function 2233, to the overall control server 10. In this situation, the content of the state information is not particularly limited, and various types of information may be included.

For example, the state information transmitting function 2235 may include, in the state information, a result of counting the number (quantity) of pieces of medical data used in the machine learning process. Further, the state information transmitting function 2235 may include, in the state information, a result of counting the number of pieces of medical data used in the machine learning process for each of various attributes of the patients (hereinafter "patient attributes") related to the medical data. The patient attributes denote, for example, the gender, the age (an age group), the weight, and the like and do not include information that makes it possible to identify individual persons.

Further, for example, the state information transmitting function 2235 may include, in the state information, an evaluation value of the model (the prototype model). In this situation, the evaluation value denotes an evaluation value of a trained model obtained by using a model currently being created as the trained model. More specifically, the evaluation value denotes, for example, a ratio of correct incidents indicating the ratio by which inferred results obtained by inputting learning-purpose medical data (e.g., image data) to the trained model coincide with diagnosis results of the training data.

What calculates the evaluation value and the timing of the calculation are not particularly limited. The evaluation value may be calculated as one step of the machine learning process. For example, the evaluation value of the trained model may be calculated every time the change amount calculating function 2233 has machine-learned one hundred samples, by temporarily using the model at that stage as a trained model. In that situation, the medical data used for the calculation of the evaluation value may be medical data that has already been machine-learned or may be medical data that has not been used in machine learning.

Further, the timing and the transmission method used by the state information transmitting function 2235 to transmit the state information are not particularly limited, either. For example, the state information transmitting function 2235 may transmit the state information with the same timing as that used by the change amount transmitting function 2234 for transmitting the change amount ΔW. Alternatively, the state information transmitting function 2235 may transmit the state information in response to a request from the overall control server 10.

Figure 4:
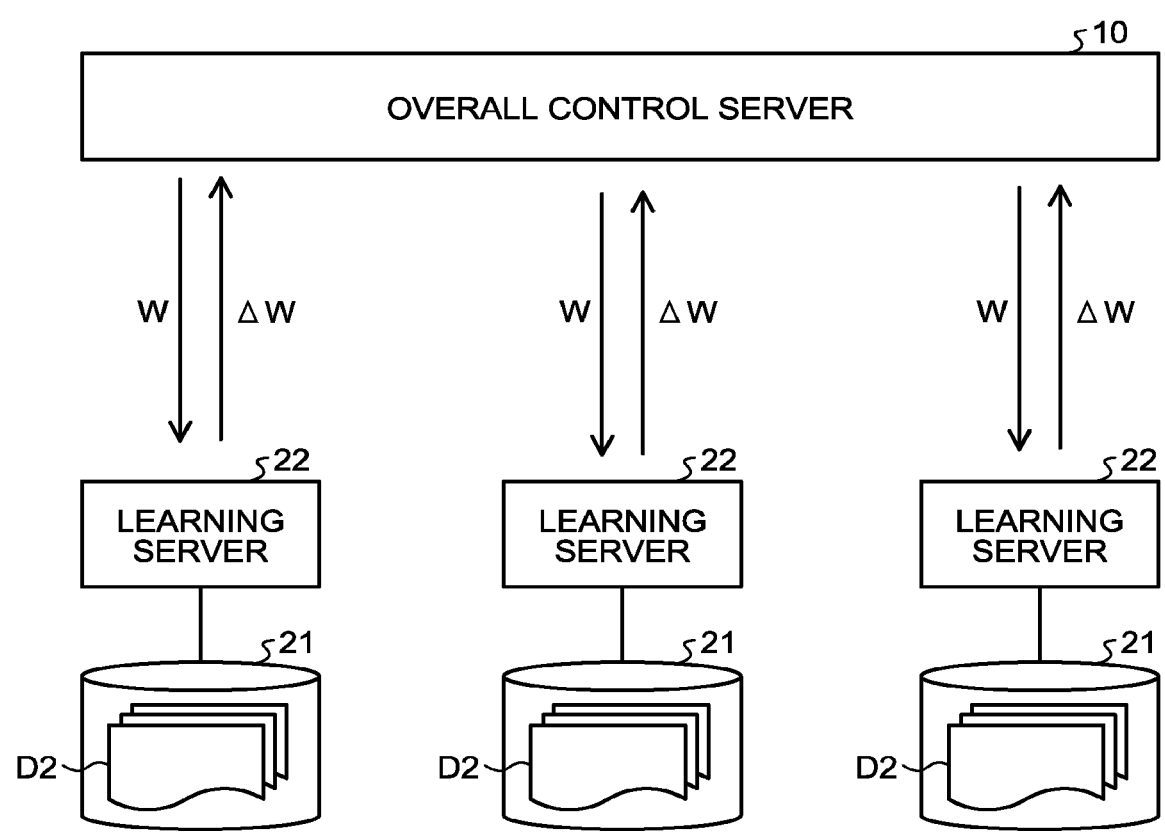
FIG. 4 is a drawing for explaining operations related to a machine learning process of the overall control server and the learning servers according to the embodiment.

Next, operations related to a machine learning process of the overall control server 10 and the learning servers 22 will be explained, with reference to FIG. 4. FIG. 4 is a drawing for explaining the operations related to the machine learning process of the overall control server 10 and the learning servers 22.

At first, in each of the learning servers 22 where the machine learning execution environment has been realized by the learning-purpose program D1, a machine learning process is performed by using medical data D2 managed by the data managing apparatus 21.

More specifically, in each of the learning servers 22, the parameter receiving function 2232 receives a weight coefficient W transmitted thereto from the overall control server 10. On the basis of the weigh coefficient W, the change amount calculating function 2233 performs the machine learning process by applying the medical data D2 read from the data managing apparatus 21 to the model. Further, the change amount calculating function 2233 calculates a change amount ΔW of the weight coefficient W, regarding a change caused by the execution of the machine learning process. After that, the calculated change amount ΔW is transmitted to the overall control server 10 by the change amount transmitting function 2234.

Further, in the overall control server 10, when the change amount receiving function 152 receives the change amount ΔW transmitted thereto from any of the learning servers 22, the parameter adjusting function 153 determines a new weight coefficient W on the basis of the change amount ΔW. The parameter transmitting function 154 transmits the weight coefficient W determined by the parameter adjusting function 153 to the learning server 22 that transmitted the change amount ΔW.

As a result of the overall control server 10 and the learning servers 22 repeatedly performing the abovementioned process, the machine learning process individually progresses in each of the learning servers 22. Further, when it is determined that the learning process is completed, the parameter adjusting function 153 determines, for example, an average value or a weighted average value of the weight coefficients W held in the learning servers 22 as a final learning result. The learning result (a weight coefficient W) determined in this situation will serve as a parameter that is used in common to trained models each of which is created by a different one of the learning servers 22. In other words, in the medical information processing system 1, by repeatedly performing the process described above, it is possible to perform the machine learning process integrating the medical data D2 managed by each of the hospitals, without taking the medical data D2 to the outside.

The method for determining whether the learning process is completed is not particularly limited and may arbitrarily be set. For example, the completion of the learning process may be determined, when the condition is satisfied that the total number of pieces of medical data used in the machine learning process in each of the learning servers 22 has reached a predetermined threshold value. Alternatively, an operation being input via the input interface 130 and instructing that the learning process be completed may be used as a trigger.

In relation to this, in the medical information processing system 1 described above, because the medical data D2 used in the machine learning process is independently acquired by each of the hospitals, there is a possibility that the numbers of pieces of medical data D2 and the patient attributes related to the medical data D2 may vary among the hospitals.

For example, when the number of pieces of medical data D2 at a specific hospital is larger than the numbers of pieces of medical data D2 at the other hospitals, the learning result from the specific hospital may be dominant, and there is a possibility that the derived learning result may be optimized for that hospital. In another example, when the number of pieces of medical data D2 related to the patients in a specific age group is larger than the numbers of pieces of medical data D2 related to the patients in the other age groups, the learning result related to the patients in the specific age group may be dominant, and there is a possibility that the derived learning result may be optimized for the patients in that age group.

To cope with these situations, the overall control server 10 is configured to cause the abovementioned display controlling function 156 to display the learning state at each of the hospitals (in each of the learning servers 22) in such a manner that comparison is possible. Further, by employing the abovementioned correcting function 157, the overall control server 10 is configured to provide an environment in which it is possible to correct unevenness in the numbers of pieces of data. In the following sections, operations performed by the display controlling function 156 and the correcting function 157 will be explained.

Figure 5:
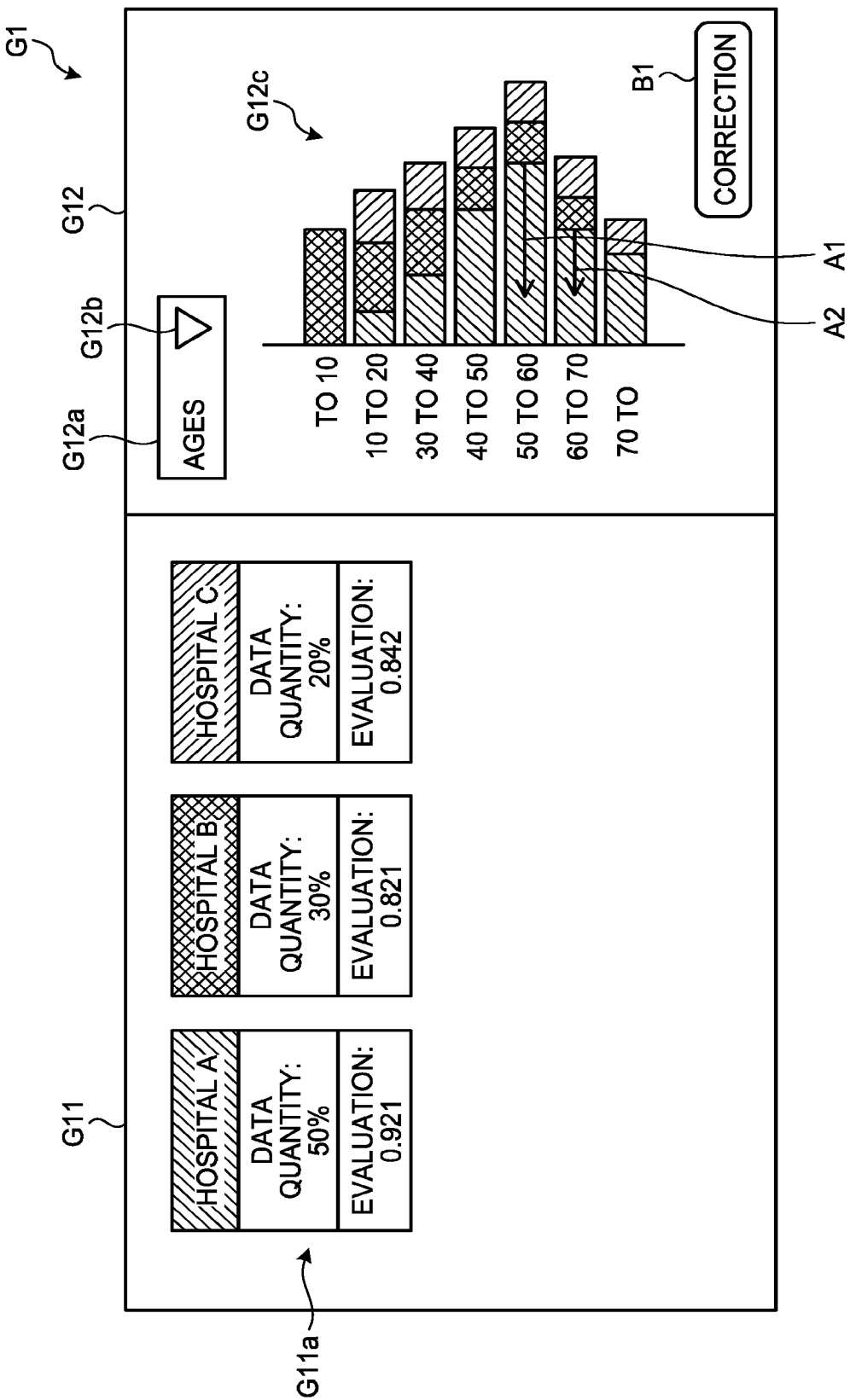
FIG. 5 is a drawing illustrating an example of a state screen displayed by a display controlling function according to the embodiment.

The display controlling function 156 is configured to cause the display 140 to display a state screen illustrated in FIG. 5, for example, on the basis of the state information of each of the learning servers 22 received by the state information receiving function 155.

FIG. 5 is a drawing illustrating the example of the state screen displayed by the display controlling function 156. As illustrated in FIG. 5, a state screen G1 includes a first display region G11 on the left side of the screen and a second display region G12 on the right side of the screen. The first display region G11 displays basic information G11a indicating the state of the learning process at each of the hospitals. For example, FIG. 5 illustrates an example in which, as the basic information G11a, a percentage ("DATA QUANTITY") of the number of pieces of data at each hospital, relative to a total number of pieces of data is displayed together with an evaluation value. With this arrangement, by viewing the first display region G11, the operator of the overall control server 10 is able to easily recognize what learning state each of the learning servers 22 provided at the hospitals is in.

Further, the second display region G12 displays a breakdown of the medical data used in the machine learning process at each the hospitals, for each of the patient attributes. More specifically, the second display region G12 has a setting region G12a used for setting a patient attribute. In the setting region G12a, by operating an operator G12b, it is possible to select an arbitrary attribute. FIG. 5 illustrates an example in which the ages are selected (set) as the patient attribute.

The display controlling function 156 is configured to display the percentage of the number of pieces of data at each hospital, relative to the total number of pieces of medical data used at the hospitals, in units of the attribute set in the setting region G12a. For example, when the ages are set in the setting region G12a, a graph G12c is displayed to indicate, for each of the age groups, the percentage of the number of pieces of data at each of the hospitals relative to the total number of pieces of medical data used at the hospitals.

FIG. 5 illustrates the example in which, for each of the age groups spanning ten years of age, the percentage of the number of pieces of data at each of the hospitals is expressed by using a bar graph (stacked bar graph) format. The hatching patterns in the sectioned regions of the bars correspond to the hatching patterns of the hospitals displayed in the first display region G11. Further, the sizes of the sectioned regions of the bars indicate the percentages of the numbers of pieces of data at the corresponding hospitals. With this arrangement, by viewing the second display region G12 (the graph G12c), the operator of the overall control server 10 is able to easily recognize the breakdown of the medical data used in the machine learning process at each of the hospitals.

In the example in FIG. 5, from what is displayed in the first display region G11, it is observed that the percentage of the number of pieces data at hospital A is higher than those at the other hospitals, namely hospitals B and C. Further, for example, from what is displayed in the second display region G12, it is observed that the numbers of pieces of data at hospital A are uneven in specific age groups. As explained above, when the numbers of pieces of data are uneven, there is a possibility that the created model may be optimized for the environment at hospital A or for the specific age groups.

In that situation, by employing the correcting function 157, the overall control server 10 is capable of correcting the unevenness in the numbers of pieces of data. In response to an operation performed via the input interface 130, the correcting function 157 performs a process to correct the numbers of pieces of medical data used in the learning process.

For example, when operations (operations A1 and A2 or the like in FIG. 5) to reduce the percentage of a specific hospital included in the bars of specific age groups are performed, and subsequently, a correction button B1 provided in the second display region G12 is operated, the correcting function 157 determines that it is instructed that the numbers of pieces of data be changed. In that situation, the correcting function 157 performs a process of reducing the numbers of pieces of medical data used in the machine learning process at the specific hospital designated in the operation, to the number of pieces of data corresponding to the percentage after the reducing operation.

More specifically, the correcting function 157 transmits, to the learning server 22 at the hospital designated in the operation, instruction information that limits the number of pieces of medical data used in the machine learning process, to the number of pieces of data corresponding to the percentage after the reducing operation. For instance, in the example in FIG. 5, the correcting function 157 transmits, to the learning server 22 at hospital A, instruction information indicating that the numbers of pieces of medical data related to the age groups 50's and 60's be reduced to the numbers of pieces of data corresponding to the percentages after the reducing operation.

Upon receipt of the instruction information, the change amount calculating function 2233 of the learning server 22 performs a machine learning process in which the number of pieces of medical data read from the data managing apparatus 21 is limited to the number of pieces of data instructed in the instruction information. In this situation, in accordance with the instruction information, the change amount calculating function 2233 may be configured to re-execute the machine learning process with the first-time medical data by using the model (the prototype model) in the initial state or may be configured to re-execute the machine learning process with the first-time medical data by using a model that has progressed in the machine learning.

Further, the percentage changing operation via the graph G12c, i.e., the operation to change the number of pieces of data, does not necessarily have to be performed in the reducing direction and may be performed in the increasing direction. In that situation, with respect to the learning server 22 at the hospital designated in the operation, the correcting function 157 performs a process of increasing the number of pieces of medical data used in the learning process, to the number of pieces of data corresponding to the percentage after the increasing operation.

More specifically, the correcting function 157 transmits, to the learning server 22 at the hospital designated in the operation, instruction information indicating that the number of pieces of medical data used in the learning process be increased to the number of pieces of data corresponding to the percentage after the increasing operation. Upon receipt of the instruction information, the change amount calculating function 2233 of the learning server 22 performs a learning process in which the number of pieces of medical data read from the data managing apparatus 21 is increased up to the number of pieces of data instructed in the instruction information. In this situation, the change amount calculating function 2233 can continue to perform the learning process by using the model that has progressed in the learning.

When the number of pieces of data is increased, the number of pieces of medical data held at the designated hospital may not be sufficient for the number of pieces of data after the increasing operation. In that situation, for example, the correcting function 157 may be configured to read as many pieces of anonymized sample data that do not belong to any hospital as the number of pieces of data that are lacking and to offer the read pieces of sample data to the learning server 22 at the designated hospital. In this situation, the sample data has the same data configuration as that of the medical data used at each hospital in the learning process. In correspondence with each of the patient attributes, a plurality of pieces of sample data are stored (prepared) in a storage, such as the storage 120.

In the learning server 22, upon receipt of the sample data, the introducing function 2231, for example, is configured to store the sample data into the data managing apparatus 21. With this arrangement, the learning server 22 is able to use the sample data stored in the data managing apparatus 21 for the learning process, similarly to the existing medical data.

Figure 6:
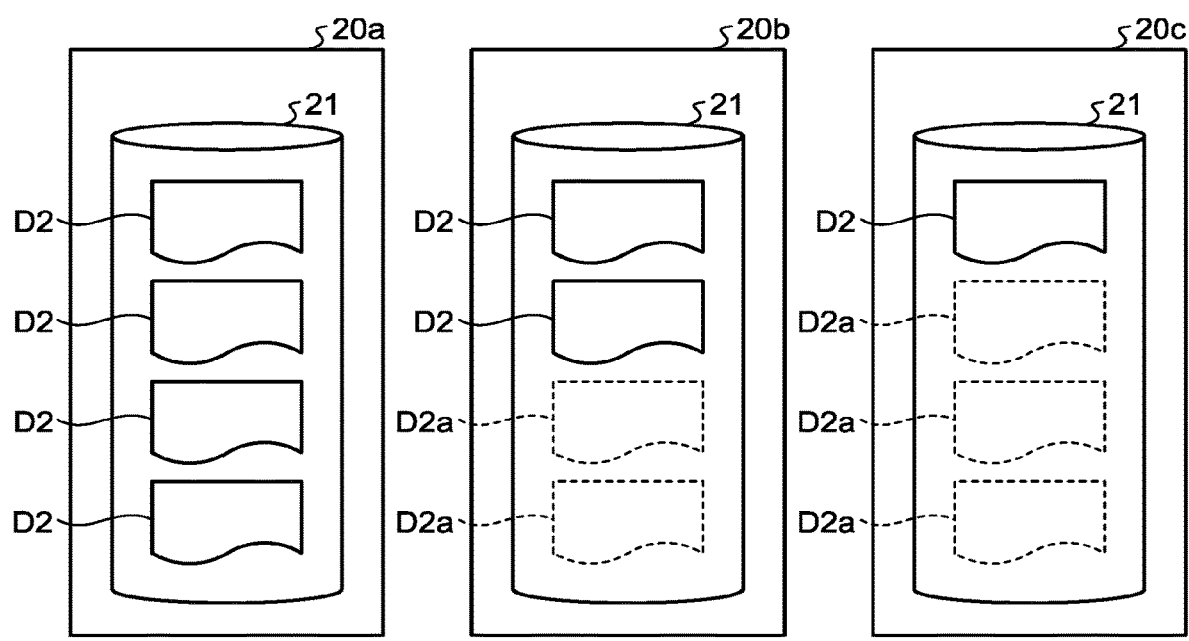
FIG. 6 is a drawing for explaining an operation performed by a correcting function according to the embodiment.

FIG. 6 is a drawing for explaining an operation performed by the correcting function 157 and illustrates an example of the operation in which the number of pieces of data is increased. The data managing apparatus 21 provided in each of the medical institution systems 20a to 20c is configured to store therein the learning-purpose medical data D2 acquired at the host hospital. FIG. 6 illustrates an example in which the data managing apparatus 21 in the medical institution system 20a stores therein four pieces of medical data D2; the data managing apparatus 21 in the medical institution system 20b stores therein two pieces of medical data D2; and the data managing apparatus 21 in the medical institution system 20c stores therein one piece of medical data D2.

In this situation, for example, let us discuss an example in which the overall control server 10 has performed an operation to increase the number of pieces of data in each of the medical institution systems 20b and 20c to "4". In that situation, with respect to the medical institution system 20b, the correcting function 157 reads two pieces of sample data that are lacking, from the storage 120 or the like and saves the read pieces of sample data into the data managing apparatus 21 via the learning server 22. Further, with respect to the medical institution system 20c, the correcting function 157 reads three pieces of sample data that are lacking, from the storage 120 or the like and saves the read pieces of sample data into the data managing apparatus 21 via the learning server 22. FIG. 6 illustrates the sample data as pieces of medical data D2a drawn with broken lines.

With this arrangement, for example, even when there is unevenness in the number of pieces of medical data among the hospitals, it is possible to equalize the conditions related to the learning to be performed among the hospitals, with the corrections (the changing process) performed by the correcting function 157 on the numbers of pieces of data. In this situation, the pieces of sample data supplied to the medical institution systems 20b and 20c may include some duplicate data or may be mutually different.

Further, after the number of pieces of data was changed by the correcting function 157, the display controlling function 156 is configured to cause a state screen to be displayed on the basis of the state information transmitted thereto from each of the learning servers 22 in such a manner that comparison of the learning states between before the change and after the change is possible.

Figure 7:
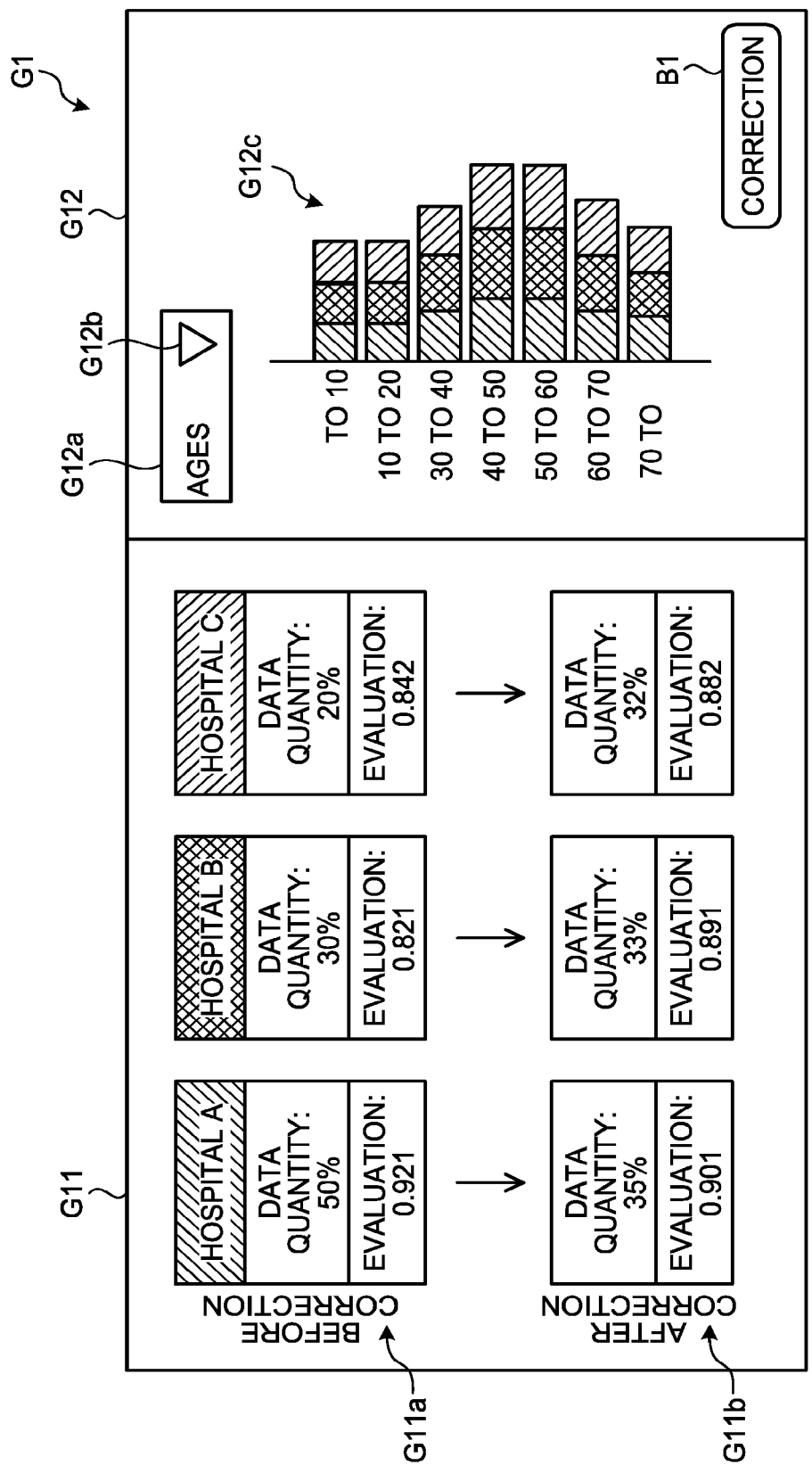
FIG. 7 is a drawing illustrating another example of the state screen displayed by the display controlling function according to the embodiment.

FIG. 7 is a drawing illustrating another example of the state screen displayed by the display controlling function 156. FIG. 7 illustrates the state screen G1 displayed on the basis of the state information after the number of pieces of data is changed by the correcting function 157.

In this situation, in the first display region G11, post-change basic information G11b is displayed, together with pre-change basic information G11a. Further, in the second display region G12, a breakdown of the post-change medical data used in the learning process at each of the hospitals is displayed. With this arrangement, by comparing the basic information G11a with the basic information G11b displayed in the first display region G11, the operator of the overall control server 10 is able to easily recognize how the learning state changed between before and after the change in the number of pieces of data. Further, by viewing the second display region G12 (the graph G12c), the operator of the overall control server 10 is able to easily recognize the breakdown of the post-change medical data used in the machine learning process at each of the hospitals.

The display mode of the state screen G1 is not limited to the examples illustrated in FIGS. 5 and 7. For instance, it is also acceptable to display the first display region G11 and the second display region G12 on mutually-different screens. Further, the graph G12c does not necessarily have to be a bar graph and may be displayed by using another graph format.

Next, an example of the abovementioned operations performed by the overall control server 10 and the learning servers 22 will be explained, with reference to FIGS. 8 to 10.

Figure 8:
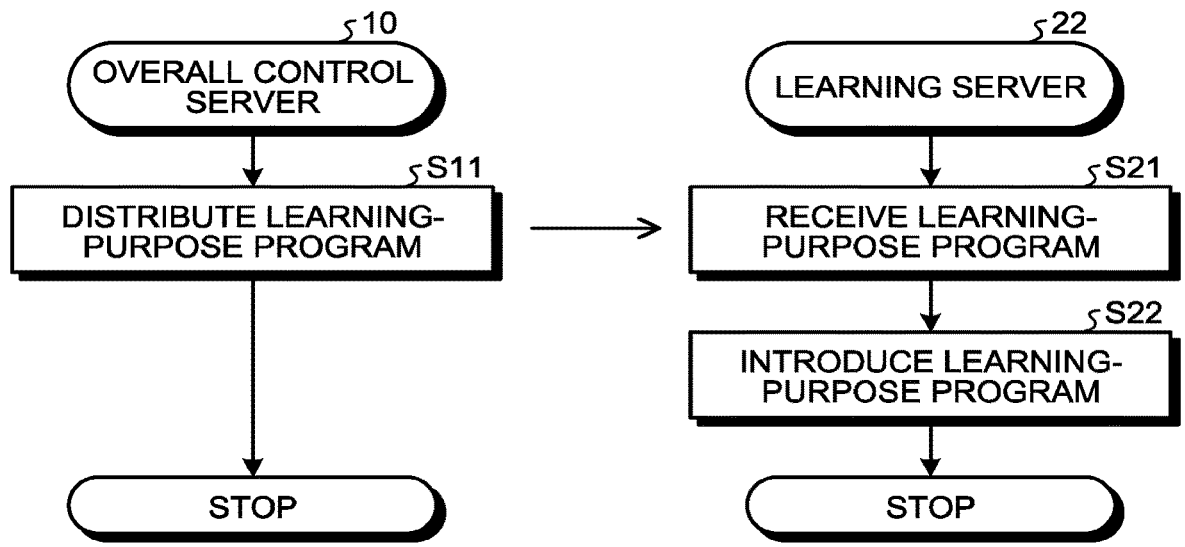
FIG. 8 is a flowchart illustrating an example of a process related to a learning-purpose program distribution performed by the overall control server and the learning servers according to the embodiment.

FIG. 8 is a flowchart illustrating an example of a process related to a learning-purpose program distribution performed by the overall control server 10 and any of the learning servers 22. At first, the distributing function 151 of the overall control server 10 distributes the learning-purpose program D1 stored in the storage 120 to each of the learning servers 22 connected to the network N1 (step S11).

Further, upon receipt of the learning-purpose program D1 distributed from the overall control server 10 (step S21), the introducing function 2231 of the learning server 22 stores the learning-purpose program D1 into the storage 222. After that, by introducing the learning-purpose program D1 to the host device thereof (step S22), the introducing function 2231 realizes an environment in which the machine learning process is executable.

Figure 9:
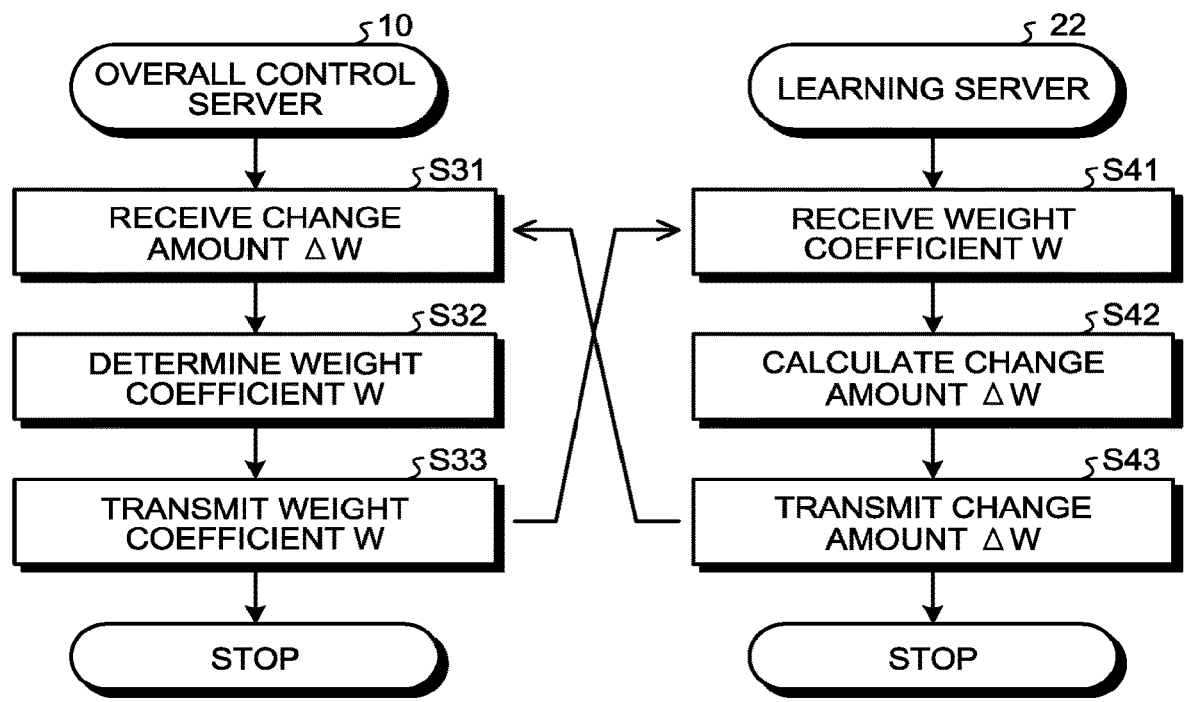
FIG. 9 is a flowchart illustrating an example of a process related to a machine learning process performed by the overall control server and the learning servers according to the embodiment.

FIG. 9 is a flowchart illustrating an example of a process related to a machine learning process performed by the overall control server 10 and the learning servers 22. At first, the change amount receiving function 152 of the overall control server 10 receives a change amount $\Delta W$ from any of the learning servers 22 (step S31). On the basis of the change amount $\Delta W$ received at step S31, the parameter adjusting function 153 determines a new weight coefficient W (step S32). Subsequently, the parameter transmitting function 154 transmits the weight coefficient W determined at step S32 to the learning server 22 that transmitted the change amount $\Delta W$ (step S33).

Further, in the learning server 22, the parameter receiving function 2232 receives the weight coefficient W transmitted thereto from the overall control server 10 (step S41). On the basis of the weight coefficient W received at step S41, the change amount calculating function 2233 calculates a change amount $\Delta W$ by performing a machine learning process by using the learning-purpose medical data (step S42). After that, the change amount transmitting function 2234 transmits the change amount $\Delta W$ calculated at step S42 to the overall control server 10 (step S43).

Further, as a result of the processes at steps S31 to S33 and steps S41 to S43 being repeatedly performed, the machine learning process individually progresses in each of the learning servers 22.

Figure 10:
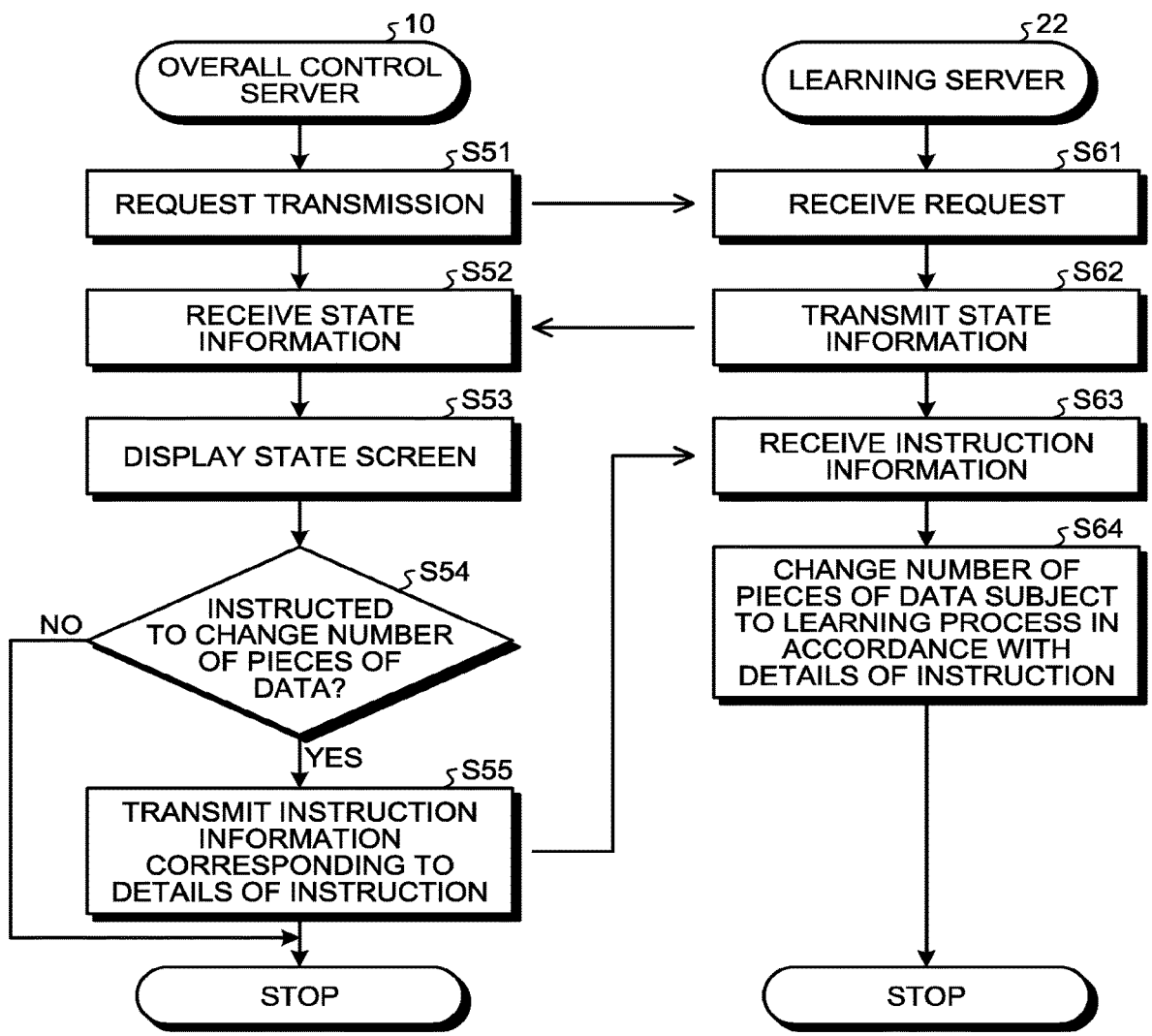
FIG. 10 is a flowchart illustrating examples of processes related to displaying the state of machine learning processes and correcting the numbers of pieces of data performed by the overall control server and the learning servers according to the embodiment.

FIG. 10 is a flowchart illustrating examples of processes related to displaying the state of decentralized machine learning processes and correcting learning conditions performed by the overall control server 10 and the learning servers 22. In the present processes, a mode will be explained in which each of the learning servers 22 transmits the state information in response to a request from the overall control server 10.

At first, when a predetermined operation (e.g., an operation instructing that a state screen be displayed) is performed via the input interface 130, the state information receiving function 155 of the overall control server 10 requests each of the learning servers 22 to transmit state information (step S51).

In each of the learning servers 22, upon receipt of the state information transmission request (step S61), the state information transmitting function 2235 transmits the state information indicating the learning state of the host learning server 22 thereof, to the overall control server 10 (step S62).

The state information receiving function 155 of the overall control server 10 receives the state information transmitted thereto from each of the learning servers 22 (step S52). Subsequently, on the basis of the state information received at step S52, the display controlling function 156 causes the display 140 to display the state screen (step S53).

Subsequently, the correcting function 157 judges whether or not an operation instructing that the learning condition (the number of pieces of data) be changed has been received via the input interface 130 (step S54). When no change instruction is received (step S54: No), the present process is ended. On the contrary, when a change instruction is received (step S54: Yes), the correcting function 157 transmits instruction information corresponding to the details of the instruction to the learning server 22 subject to the change (step S55).

In the learning server 22, upon receipt of the instruction information transmitted from the overall control server 10 (step S63), the change amount calculating function 2233 changes the number of pieces of medical data subject to the machine learning process in accordance with the details of the instruction information (step S64), and the present process is ended.

As explained above, in the medical information processing system 1 according to the present embodiment, as a result of the overall control server 10 distributing the learning-purpose program D1 to each of the learning servers 22 respectively provided at the hospitals, the environment in which the machine learning process is executable is realized in each of the learning servers 22. Accordingly, the overall control server 10 is able to realize the execution environment that is mutually the same among the learning servers 22, without the need to tune the execution environment or the parameter for each of the learning servers 22. Consequently, the medical information processing system 1 is able to efficiently perform the machine learning processes using the medical data held at the plurality of medical institutions.

Further, in the medical information processing system 1, as a result of the overall control server 10 and the learning servers 22 exchanging the parameter (the weight coefficients W) and the change amounts of the parameter (the change amounts ΔW), it is possible to cause the machine learning process to progress individually in each of the learning servers 22. Accordingly, in the medical information processing system 1, it is possible to efficiently perform the machine learning processes integrating the medical data, without taking the medical data managed at each hospital to the outside.

Further, the overall control server 10 is configured to acquire the state information from each of the learning servers 22 and, on the basis of the state information, to cause the learning states of the learning servers 22 to be displayed in such a manner that comparison is possible. With this arrangement, the overall control server 10 is able to facilitate the comparison among the machine learning processes at the hospitals. Further, in accordance with the operation performed via the input interface 130, the overall control server 10 is configured to correct the number of pieces of medical data subject to the machine learning process in each of the learning servers 22. With this arrangement, for example, when the number of pieces of data is uneven in the machine learning process performed at a specific hospital, the overall control server 10 is able to change the number of pieces of data used in the machine learning process so as to be under the same condition as the conditions at the other hospitals. It is therefore possible to create a versatile model that is usable across the hospitals.

In the embodiments above, the example was explained in which the functional configurations of the overall control server 10 and the learning servers 22 are realized by the processing circuitry 150 and the processing circuitry 223, respectively. However, possible embodiments are not limited to this example. The functional configurations of the present disclosure may realize the functions thereof, by using only hardware or by using a combination of hardware and software.

Further, the term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processor realizes the functions by reading and executing the programs saved in the storage 120. Further, instead of saving the programs in the storage 120, it is also acceptable to directly incorporate the programs into the circuit of the processor. In that situation, the processor realizes the functions by reading and executing the programs incorporated in the circuit thereof. Further, the processor of the present embodiments does not necessarily have to be structured as a single circuit. It is also acceptable to structure one processor by combining together a plurality of independent circuits so as to realize the functions thereof.

Further, the programs executed by the processor are provided as being incorporated, in advance, in a Read Only Memory (ROM), a storage, or the like. The programs may be provided as being recorded on a computer-readable storage medium such as a Compact Disk Read-Only Memory (CD-ROM), a Flexible Disk (FD), a Compact Disk Recordable (CD-R), Digital Versatile Disk (DVD), or the like, in a file in a format that is installable or executable by these devices. Further, the programs may be stored in a computer connected to a network such as the Internet so as to be provided or distributed as being downloaded via the network. For example, the programs are structured with modules including the functional units described above. In the actual hardware, as a result of a CPU reading and executing the programs from a storage medium such as a ROM, the modules are loaded into a main storage and generated in the main storage.

According to at least one aspect of the embodiments described above, it is possible to efficiently perform the machine learning processes using the medical data held at the plurality of medical institutions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:

processing circuitry configured to
distribute, to an information processing apparatus provided at each of a plurality of medical institutions, a program configured to cause a machine learning process to be executed by using medical data held at the medical institution having the information processing apparatus;
receive, from each of the information processing apparatuses, a change amount in a parameter related to the machine learning process, regarding a change caused in conjunction with the execution of the machine learning process;
adjust a value of the parameter based on the received change amount;
transmit the adjusted parameter to each of the information processing apparatuses to cause the machine learning process to be executed based on the parameter;
receive, from each of the information processing apparatuses, (i) an evaluation value on a model created by the corresponding information processing apparatus in the machine learning process, and (ii) a quantity of pieces of medical data used for creating the model;
display the evaluation value received from each of the information processing apparatuses in such a manner that comparison is possible between before and after a change in the quantity of pieces of medical data, and display a graph indicating a percentage of the quantity of pieces of medical data received from each of the information processing apparatuses relative to a sum of the quantities of pieces of medical data received from the information processing apparatuses; and
in response to an operation to change one of the percentages indicated by the graph, instruct a designated information processing apparatus designated in the operation among the information processing apparatuses to change the quantity of pieces of medical data used by the designated information processing apparatus in the machine learning process.

2. The medical information processing apparatus according to claim 1, wherein, based on the change amount in the parameter received from each of the information processing apparatuses, the processing circuitry is further configured to determine a value of the parameter that is used in common to trained models created by the information processing apparatuses.

3. The medical information processing apparatus according to claim 1, wherein
the processing circuitry is further configured to receive a piece of state information indicating a state of the machine learning process from each of the information processing apparatuses, and
based on the received pieces of state information, the processing circuitry is further configured to cause a screen to be displayed in such a manner that comparison among the states of the machine learning processes executed by the information processing apparatuses is possible.

4. The medical information processing apparatus according to claim 1, wherein
the processing circuitry is further configured to receive, from each of the information processing apparatuses, information in which a quantity of pieces of medical data used by the corresponding information processing apparatus in the machine learning process is counted with respect to each patient attribute related to the medical data, and
the processing circuitry is further configured to cause percentages to be displayed in such a manner that comparison is possible in units of the patient attributes, the percentages each indicating a percentage of the quantity of pieces of medical data received from the corresponding information processing apparatus, relative to a total quantity of pieces of medical data received from the information processing apparatuses.

5. The medical information processing apparatus according to claim 1, wherein, in accordance with an operation instructing that the quantity of pieces of medical data be changed, the processing circuitry is further configured to instruct the information processing apparatus designated in the operation to either increase or reduce the quantity of pieces of medical data used in the machine learning process.

6. The medical information processing apparatus according to claim 5, wherein, upon receipt of the operation instructing that the quantity of pieces of medical data be reduced, the processing circuitry is further configured to instruct the information processing apparatus designated in the operation to reduce the quantity of pieces of medical data and to also re-execute the machine learning process.

7. The medical information processing apparatus according to claim 5, wherein, upon receipt of the operation instructing that the quantity of pieces of medical data be increased, the processing circuitry is further configured to instruct the information processing apparatus designated in the operation to increase the quantity of pieces of medical data and to provide sample data that does not belong to any of the medical institutions as medical data corresponding to a quantity of pieces of medical data that are lacking.

8. A medical information processing system comprising information processing apparatuses respectively provided in a plurality of medical institutions and a medical information processing apparatus configured to communicate with each of the information processing apparatuses, wherein the medical information processing apparatus includes processing circuitry configured to:
distribute, to each of the information processing apparatuses, a program configured to cause a machine learning process to be executed by using medical data held at the medical institution having the information processing apparatus;
receive, from each of the information processing apparatuses, a change amount in a parameter related to the machine learning process, regarding a change caused in conjunction with the execution of the machine learning process;
adjust a value of the parameter based on the received change amount;
transmit the adjusted parameter to each of the information processing apparatuses to cause the machine learning process to be executed based on the parameter;
receive, from each of the information processing apparatuses, (i) an evaluation value on a model created by the corresponding information processing apparatus in the machine learning process, and (ii) a quantity of pieces of medical data used for creating the model;
display the evaluation value received from each of the information processing apparatuses in such a manner that comparison is possible between before and after a change in the quantity of pieces of medical data, and display a graph indicating a percentage of the quantity of pieces of medical data received from each of the information processing apparatuses relative to a sum of the quantities of pieces of medical data received from the information processing apparatuses; and
in response to an operation to change one of the percentages indicated by the graph, instruct a designated information processing apparatus designated in the operation among the information processing apparatuses to change the quantity of pieces of medical data used by the designated information processing apparatus in the machine learning process.

* * * * *